(12) United States Patent
Powell

(10) Patent No.: US 10,751,453 B2
(45) Date of Patent: Aug. 25, 2020

(54) WEARABLE MACHINE SYSTEM

(71) Applicant: Patrick Powell, Farmington Hills, CT (US)

(72) Inventor: Patrick Powell, Farmington Hills, CT (US)

(73) Assignee: Arbor Grace, Inc., Detroit, MI (US)

( * ) Notice: Subject to any disclaimer, the term of this patent is extended or adjusted under 35 U.S.C. 154(b) by 1292 days.

(21) Appl. No.: 14/676,221

(22) Filed: Apr. 1, 2015

(65) Prior Publication Data
US 2016/0287768 A1    Oct. 6, 2016

(51) Int. Cl.
*A61M 1/06* (2006.01)
*A61M 1/00* (2006.01)
*A61M 1/10* (2006.01)

(52) U.S. Cl.
CPC .......... *A61M 1/064* (2014.02); *A61M 1/0023* (2013.01); *A61M 1/0088* (2013.01); *A61M 1/06* (2013.01); *A61M 1/0066* (2013.01); *A61M 1/1003* (2014.02); *A61M 2205/10* (2013.01); *A61M 2205/3303* (2013.01); *A61M 2205/8281* (2013.01); *A61M 2209/088* (2013.01)

(58) Field of Classification Search
CPC .... A61M 1/06; A61M 1/0023; A61M 1/0088; A61M 1/003; A61M 1/0066; A61M 2205/8275; A61M 2205/8281; A01J 5/047
See application file for complete search history.

(56) References Cited

U.S. PATENT DOCUMENTS

| | | | | |
|---|---|---|---|---|
| 4,202,212 A | * | 5/1980 | Allen | G01N 1/24 417/234 |
| 4,215,689 A | * | 8/1980 | Akiyama | A61M 5/14244 128/DIG. 12 |
| 4,986,791 A | * | 1/1991 | Alfaro | A63H 3/14 446/361 |
| 2008/0208116 A1 | * | 8/2008 | Dao | A61M 1/06 604/74 |

OTHER PUBLICATIONS

International Preliminary Report on Patentability for PCT/US2016/025114 dated Oct. 12, 2017.

* cited by examiner

*Primary Examiner* — Laura A Bouchelle
*Assistant Examiner* — Justin L Zamory
(74) *Attorney, Agent, or Firm* — Carlson, Gaskey & Olds, P.C.

(57) ABSTRACT

A wearable machine system includes a garment and a passive actuator mounted to the garment. The passive actuator is actuatable in response to involuntary movements of a wearer of the garment. A machine is coupled with the passive actuator such that actuation of the passive actuator responsive to the involuntary movements mechanically drives the machine.

19 Claims, 7 Drawing Sheets

WEARABLE MACHINE SYSTEM

BACKGROUND

Pumps may be used for a variety of purposes, including biological purposes. For example, manual or battery-powered vacuum pump systems may be used for expressing and collecting milk. Vacuum pump systems may also be used for negative-pressure wound therapy to provide reduced pressure at a wound site to facilitate healing.

SUMMARY

A wearable machine system according to an example of the present disclosure includes a garment, and a passive actuator mounted to the garment. The passive actuator is actuatable in response to involuntary movements of a wearer of the garment. A machine is coupled with the passive actuator such that actuation of the passive actuator responsive to the involuntary movements mechanically drives the machine.

In a further embodiment of any of the foregoing embodiments, the passive actuator includes a cord mounted on the garment. The cord has first and second ends spanned by a cord length. The first end is fixed to the garment at an anchor point. The cord length wraps at least partially around the wearer. The second end is coupled to the machine such that the involuntary movement causes the cord to actuate the machine.

In a further embodiment of any of the foregoing embodiments, in addition to the cord length wrapping at least partially around the wearer, the cord includes at least one loop.

In a further embodiment of any of the foregoing embodiments, the garment includes an elongated strap having opposed, connectable ends, and the cord runs in the elongated direction of the elongated strap.

In a further embodiment of any of the foregoing embodiments, the anchor point is in a middle one-third of the strap.

In a further embodiment of any of the foregoing embodiments, the cord includes a wire and a sheathing. The wire is translatable inside the sheathing.

In a further embodiment of any of the foregoing embodiments, the passive actuator includes a cord mounted on the garment. The cord has first and second ends spanned by a cord length. The first end is coupled to a first portion of the machine and the second end is coupled to a second portion of the machine such that the involuntary movement causes the cord to actuate the machine In a further embodiment of any of the foregoing embodiments, the passive actuator includes first and second cords mounted on the garment. The first and second cords each include first and second ends spanned by a cord length. The first end is fixed to the garment at an anchor point. The cord length wraps at least partially around the wearer, and the second end is connected to the machine. The respective cord lengths wrap in opposite directions around the wearer such that the involuntary movements cause the first and second cords to cooperatively actuate the machine.

In a further embodiment of any of the foregoing embodiments, the respective first ends of the first and second cords are fixed at a common anchor point.

In a further embodiment of any of the foregoing embodiments, the machine includes a suction line, and actuation of the machine causes a negative pressure in the suction line.

In a further embodiment of any of the foregoing embodiments, the suction line further includes a suction cup.

A further embodiment of any of the foregoing embodiments includes a drain line and a reservoir. The drain line opens at one end to the suction cup and opening at an opposed end to the reservoir.

In a further embodiment of any of the foregoing embodiments, the involuntary movements are breathing expansion/contraction.

In a further embodiment of any of the foregoing embodiments, the garment is resilient and adapted to conform with the shape of the wearer.

In a further embodiment of any of the foregoing embodiments, the machine includes a bias member biasing the machine to a home position such that upon actuation of the machine by the passive actuator away from the home position. The biasing member moves the machine back toward the home position.

In a further embodiment of any of the foregoing embodiments, the machine is a pump or a generator.

A wearable machine system according to an example of the present disclosure includes a flexible actuator adapted to wrap at least partially around, and conform with, the shape of a wearer and resiliently stretch with involuntary movements of the wearer. A machine is coupled to be driven by the flexible actuator such that the involuntary movements of the wearer power the machine through the flexible actuator.

In a further embodiment of any of the foregoing embodiments, the involuntary movements of the wearer exclusively power the machine.

In a further embodiment of any of the foregoing embodiments, the flexible actuator includes a flexible garment with at least one translatable cord that is connected to the machine.

In a further embodiment of any of the foregoing embodiments, the machine is a vacuum pump that is connected with a suction line having a suction cup.

A method of powering a machine according to an example of the present disclosure includes wrapping a flexible actuator at least partially around a wearer such that the flexible actuator is in conformance with the shape of the wearer, and powering a machine that is coupled to the flexible actuator by resiliently stretching the flexible actuator with involuntary movements of the wearer.

In a further embodiment of any of the foregoing embodiments, the involuntary movements are breathing expansion/contraction.

BRIEF DESCRIPTION OF THE DRAWINGS

The various features and advantages of the present disclosure will become apparent to those skilled in the art from the following detailed description. The drawings that accompany the detailed description can be briefly described as follows.

DETAILED DESCRIPTION

Figure 1:
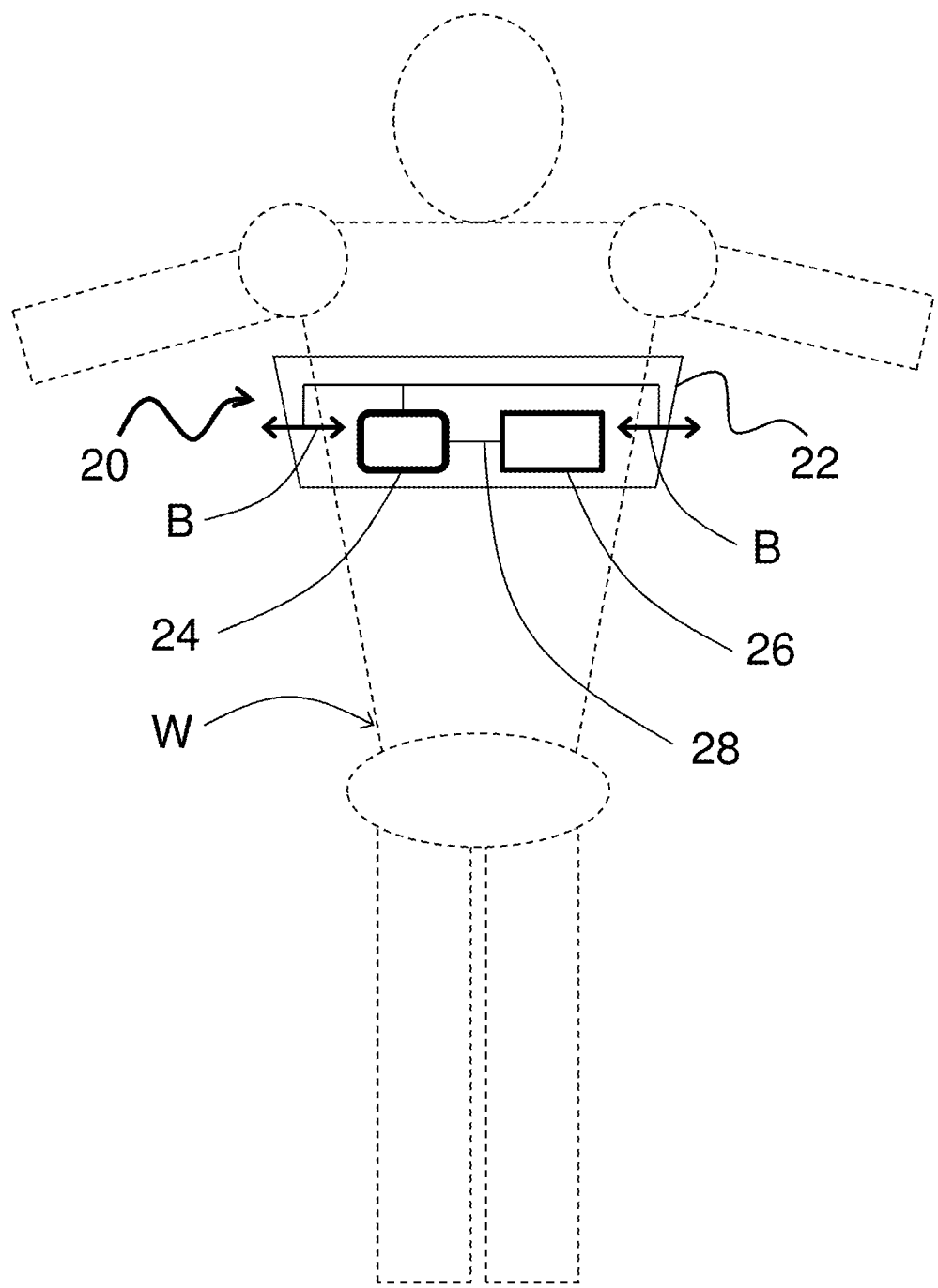
FIG. 1 illustrates an example wearable machine system.

FIG. 1 illustrates an example wearable machine system 20 (hereafter "system 20"), shown on a user or "wearer," represented at W. Although the wearer W is shown as a human form, it is to be understood that the examples herein are applicable to farm animals and other biological forms.

Humans and other biological forms may use or be subjected to using manual or battery-powered systems for various purposes, including systems for expressing and collecting milk, negative-pressure wound therapy, and the like. However, such systems require either selective manual actuation or battery power actuation. As will be described in further detail herein, the system 20 utilizes a passive, flexible actuator that uses involuntary movements of the wearer W to power a machine, such as a pump or generator, without the need for selective manual actuation (hands-free) or battery power actuation.

In the illustrated example, the system 20 includes a garment 22, a passive actuator 24, and a machine 26. Here, the garment 22 is worn around the chest of the wearer W, which involuntarily expands and contracts with breathing of the wearer W. For example, the garment 22 may be, but is not limited to, a brassiere, a sleeve, a shirt, a band, or the like. The garment 22 is not limited to use on the chest, and can alternatively be shaped to wear on other portions of a body for "harvesting" involuntary movements thereof to power a machine. Such involuntary movements can include, but are not limited to, breathing movement and involuntary movements associated with narcotic, neural, muscular, or psychological conditions. Generally, involuntary movements will be those processes in a body that the biological form is not conscious of controlling but which are controlled automatically by the nervous system and may or may not be in response to external stimuli.

The garment 22 conforms to the shape of the wearer W such that the breathing expansion/contraction or other involuntary movement of the wearer W exerts a force on the garment 22, causing the garment 22 to expand and contract, as represented at B. In this regard, the garment 22 may be fabricated of a resilient fabric, patch, film, or combination thereof such that it can conform to the wearer and contract/expand with breathing movement or other involuntary movement of the wearer W.

The passive actuator 24 is mounted, such as by fasteners, adhesive, textile techniques, combinations thereof, or the like, to the garment 22. As used herein, the term "passive" or variations thereof refer to the actuator 24 being operable to output power responsive to involuntary movements of a wearer W of the garment 22, without the need for selective external manual input or selective electrical input. Thus, the garment 22 and passive actuator 24 serve as a flexible actuator that is operable to provide power responsive to the breathing or other involuntary movement of the wearer W.

The machine 26, through link 28, is coupled with the passive actuator 24. Actuation of the passive actuator 24 responsive to the breathing or other involuntary movements of the wearer W mechanically drives the machine 26. As will be described, the machine 26 can be, but is not limited to, a vacuum pump or an electrical generator. Accordingly, the system 20 may be configured to utilize the breathing other involuntary movement of the wearer W to provide mechanical power or electrical power. Mechanical power can be used to generate a vacuum for the purpose of expressing and collecting milk or negative-pressure wound therapy. Electrical power can be used to power lights, electronics, or the like that the wearer W may also be wearing. In some examples, the involuntary movements of the wearer may be used to exclusively power the machine, while in other examples, selective external power may be additionally provided to supplement the power generated by the involuntary movements.

Figure 2A:
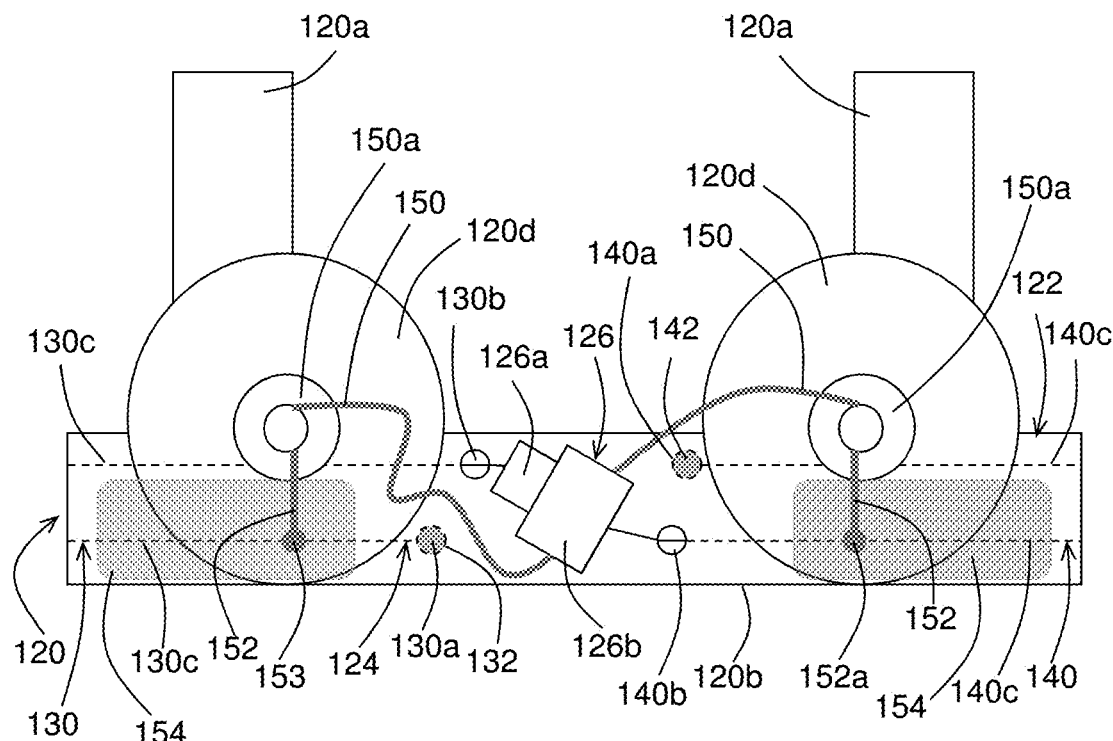
FIG. 2A illustrates a front view of another example wearable machine system based on a pump.
Figure 2B:
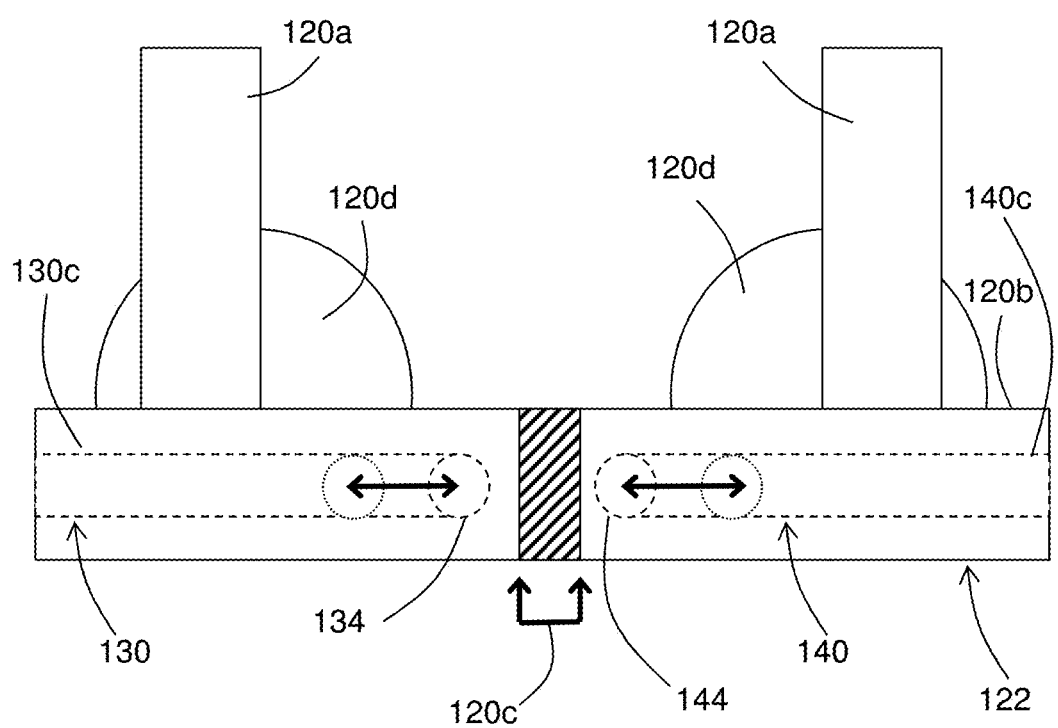
FIG. 2B illustrates a back view of the wearable machine system of FIG. 2A.

FIGS. 2A and 2B illustrate a further example of a wearable machine system 120-1. In this disclosure, like reference numerals designate like elements where appropriate and reference numerals with the addition of one-hundred or multiples thereof designate modified elements that are understood to incorporate the same features and benefits of the corresponding elements. In this example, the garment 122 of the system 120-1 is a brassiere that may include shoulder straps 120a and a horizontally elongated chest strap or band 120b with opposed connectable ends 120c (see back view FIG. 2B), and support cups 120d. At least the chest band 120b may be fabricated of a resilient fabric such that it can conform to the wearer W and contract/expand with breathing movement of the wearer W.

The passive actuator 124 includes at least one wire or cord 130 that is mounted on the garment 122. The cord 130 has first and second ends 130a/130b spanned by a cord length 130c. The first end 130a is fixed to the garment 122 at an anchor point 132.

The cord length 130c runs in the elongated direction of the chest band 120b (horizontally in the figure) and wraps at least partially around the wearer W. In this example, the cord 130 wraps around the back of the garment 122 to a location near the connectable end 120c and loops around a pivot 134. The cord 130 extends back around to the front of the garment 122, where the second end 130b of the cord 130 is coupled to the machine 126. In this example, the cord 130 includes one loop (around the pivot 134), although additional cords, loops, and pivots may be used (e.g., for movement amplification).

In this example, the machine 126 is a pump. Although one pump is shown, multiple pumps could be used. The pump includes first and second pump portions 126a/126b. The second end 130b of the cord 130 is linked to the first pump portion 126a.

In this example, the garment 122 also includes a second cord 140, which is similar to the first cord 130 but wraps in the opposite direction around the wearer W and garment 122. The second cord 140 likewise has a first end 140a fixed at an anchor point 142, a second end 140b coupled to the machine 126, and a cord length 140c that loops around a pivot 144. The second end 140b is coupled to the second pump portion 126b.

The pump may be used as a vacuum pump to express and collect milk. In this regard, the machine 126 includes one or more suction lines 150 with corresponding suction cups 150a. Drain lines 152 each open at one end to the respective one of the suction cups 150 at an opposed end to a respective reservoir 154. A one-way vacuum actuated valve 152*a* prevents milk from flowing in the reverse direction.

Figure 2C:
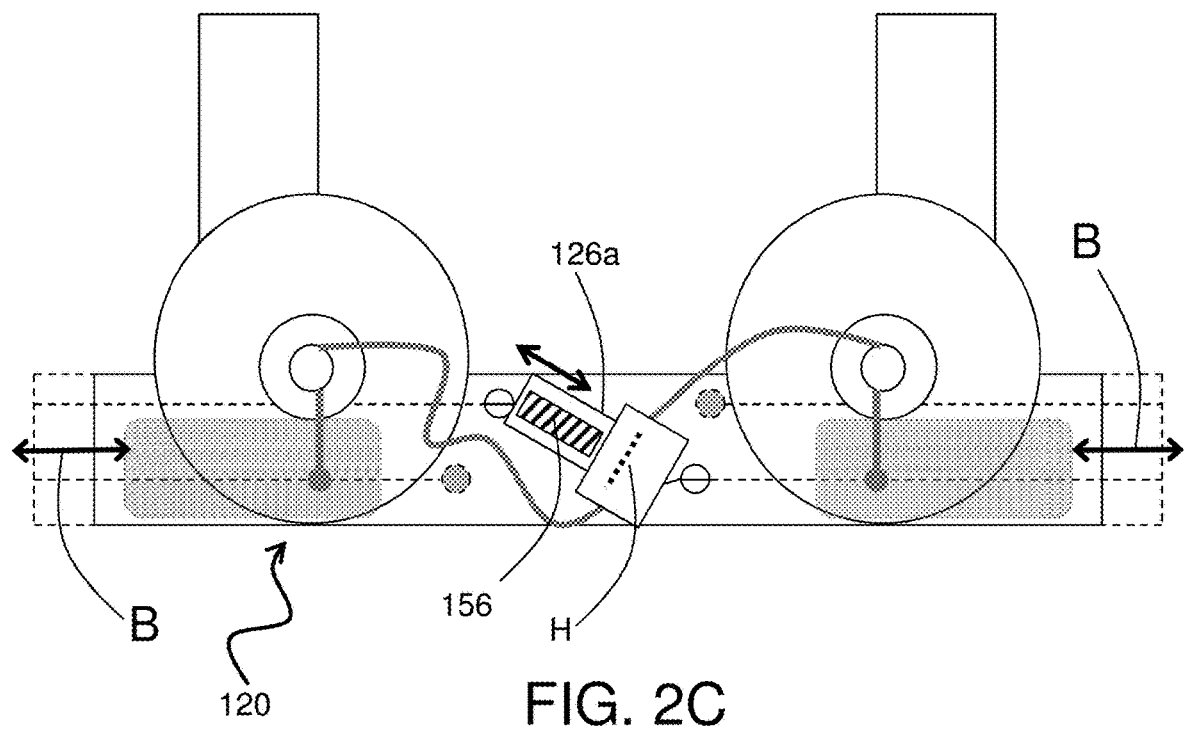
FIG. 2C illustrates operation of the wearable machine system of FIG. 2A.

FIG. 2C illustrates operation of the system 120-1. As the wearer W breathes, the garment 122 expands and contracts with the movement, causing the cords 130/140 to pull with respect to anchor points 132/142 on the pump portions 126*a*/126*b*. The pulling action mechanically actuates the pump by moving the pump portions 126*a*/126*b* relative to one another. The pump generates a negative pressure in the suction lines 150 and suction cups 150*a* to facilitate the expression of milk from the wearer W. The milk flows through drain lines 152 to the reservoirs 154. Thus, the involuntary movements of the wearer cause the cords 130/140 to cooperatively actuate the machine 126.

Optionally, the machine 126 can include a bias member 156, such as a spring, to bias the first pump portion 126*a* to a home position, represented at H. Upon actuation of the first pump portion 126*a* away from the home position, the bias member 156 moves the first pump portion 126*a* back toward the home position. For instance, the first pump portion 126*a* is a plunger or piston, and the cords 130/140 serve to extend the plunder while the bias member 156 serves to retract the plunger.

In a further example, the anchor point or points 132/142 is/are in the middle one-third of the chest band 120*b* such that the cords 130/140 loop first from front-to-back and then back-to-front around the respective pivots 134/144. The positioning in the middle one-third facilitates using a greater amount of the expansion/contraction movement of the loops of the cords 130/140. As can be appreciated though, the positioning of the cords 130/140, machine 126, and other components may be subject to other factors, such as but not limited to, the geometry of the garment 122 and wearer comfort.

Figure 3:
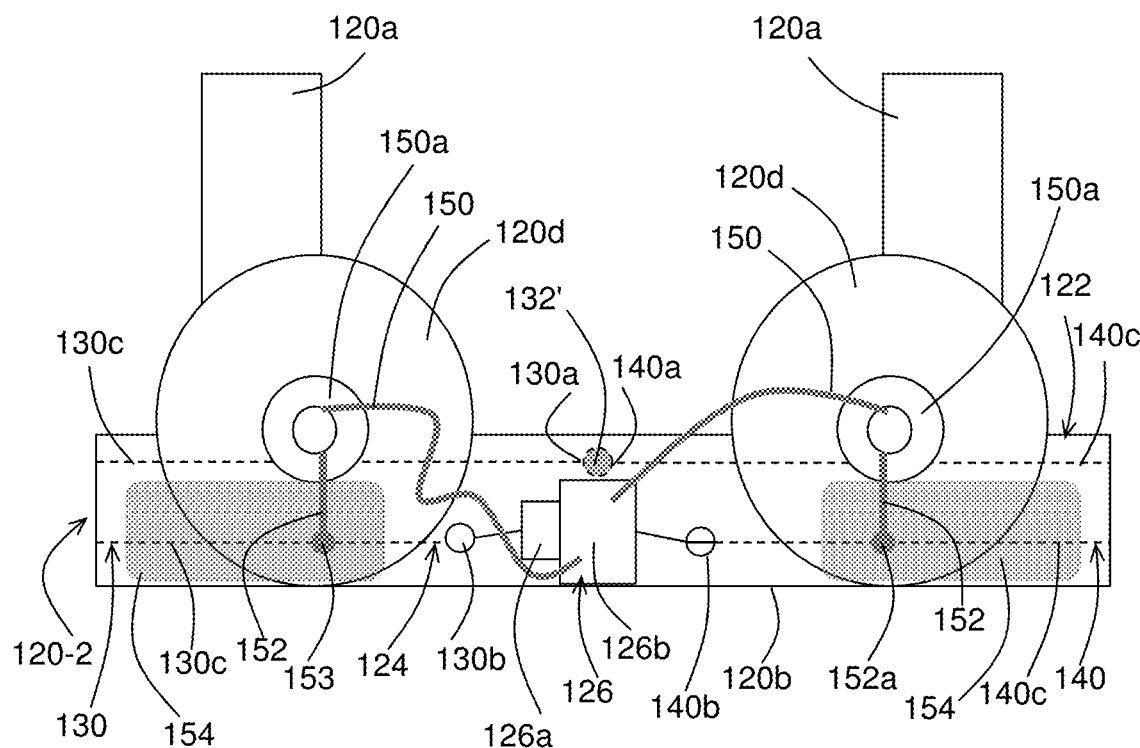
FIG. 3 illustrates a modified example of a wearable machine system that has a common anchor point for two cords.

FIG. 3 illustrates a modified system 120-2 that is the same as system 120-1 but rather than each cord 130/140 having its own anchors points 132/142, the cords 130/140 have a common anchor point 132'.

Figure 4:
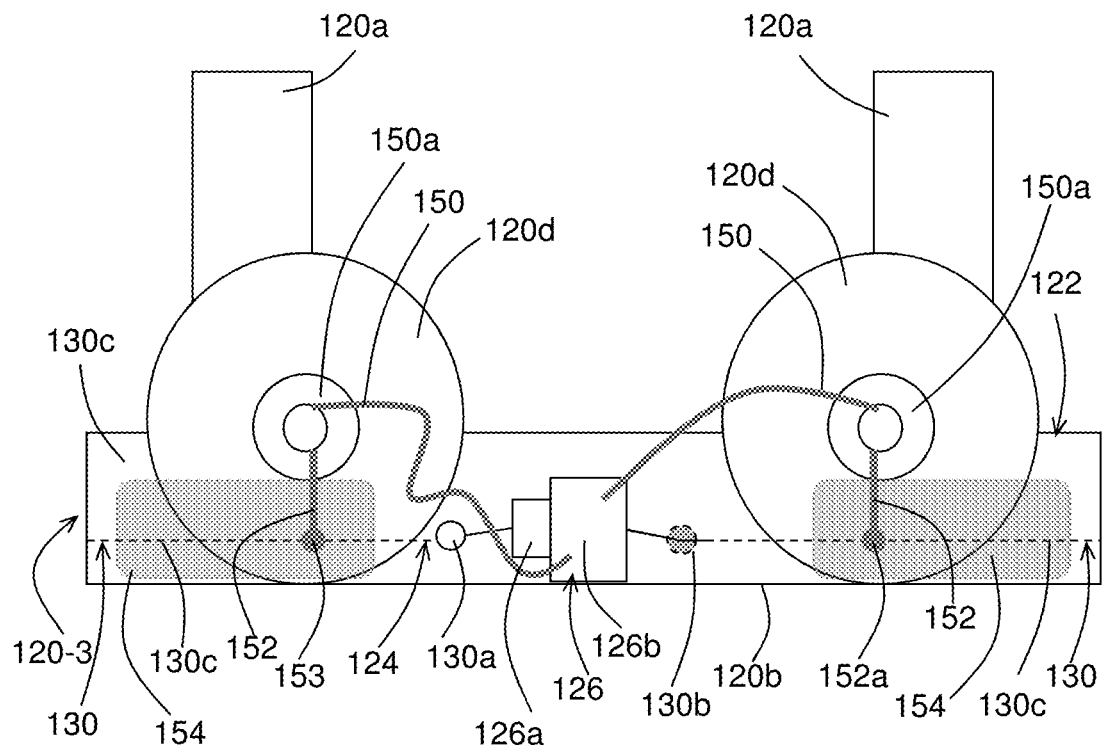
FIG. 4 illustrates another modified example of a wearable machine system that includes a single, exclusive cord.

FIG. 4 illustrates a modified system 120-3 that is the same as system 120-1 but excludes the cord 140 and thus only includes the cord 130. In this example, the first end 130*a* is linked to the first pump portion 126*a* and the second end 130*b* is linked to the second pump portion 126*b*.

Figure 5:
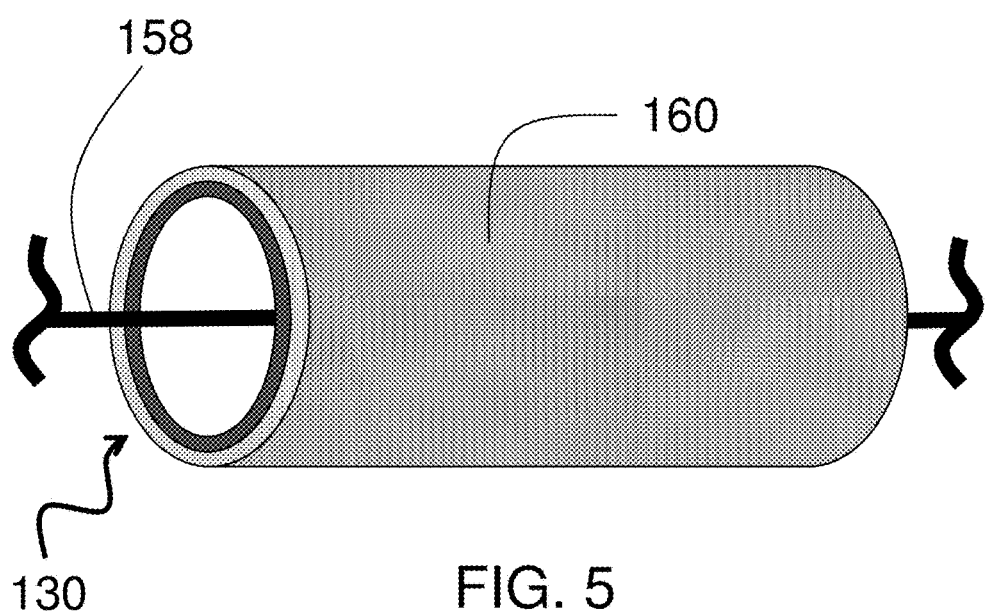
FIG. 5 illustrates an example cord for use in a wearable machine system.

FIG. 5 illustrates a representative portion of the cord 130 (or cord 140). In this example, the cord 130 includes a wire 158 and a sheathing 160. The wire 158 is translatable along its axial direction inside of the sheathing 160. In this regard, the inner diameter of the sheathing 160 may be larger than the outer diameter of the wire 158 to permit translating movement. Additionally or alternatively, the material of the sheathing 158 may be selected to provide relatively low friction with the wire 158 to facilitate low-resistance translation. The wire 158 and sheathing 160 can be sewn, fastened, bonded, or otherwise incorporated into a garment.

Figure 6:
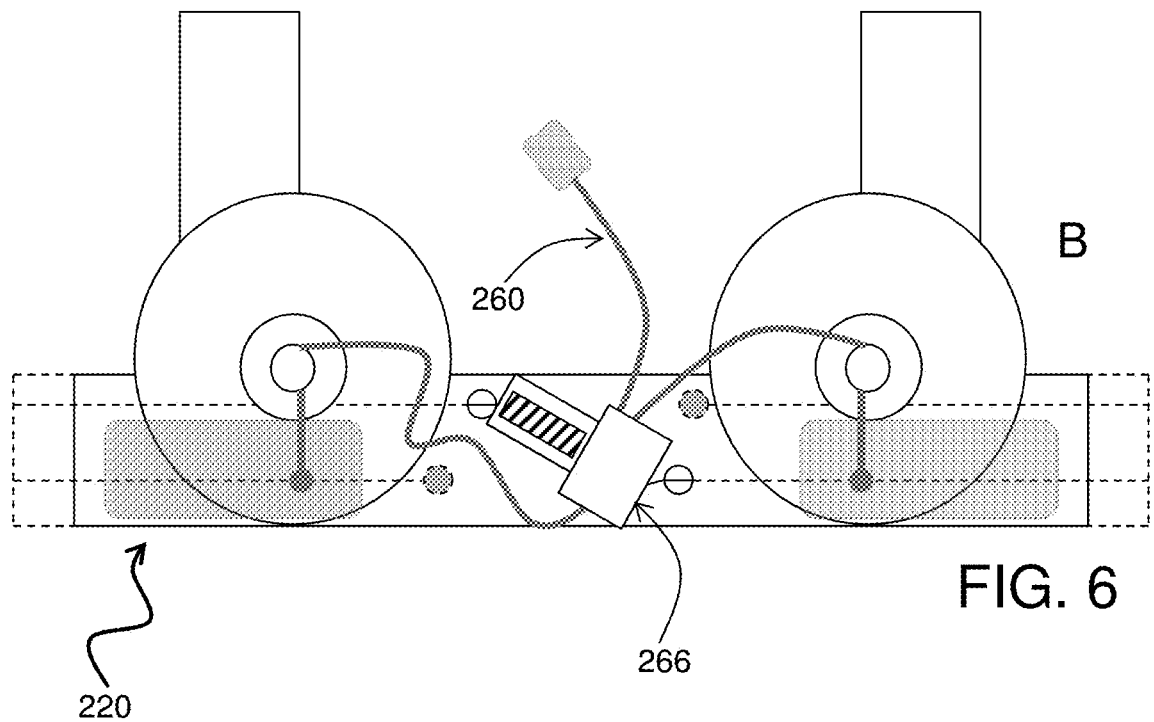
FIG. 6 illustrates another example wearable machine system with a manual pump assist.

FIG. 6 illustrates another example wearable machine system 220 that is identical to the system 120-1 but additionally includes a manual pump assist 260 connected to the machine 226 (pump). The manual pump assist 260 may be used to selectively augment the pumping of the machine 126, such as to initiate suction or to temporarily provide a stronger vacuum. However, it is to be understood that the manual pump assist 260 does not transform the system 220 from being a passive actuation system. The system 220 remains operable in response to involuntary movements without the need for selective external manual input from manual pump assist 260.

Figure 7:
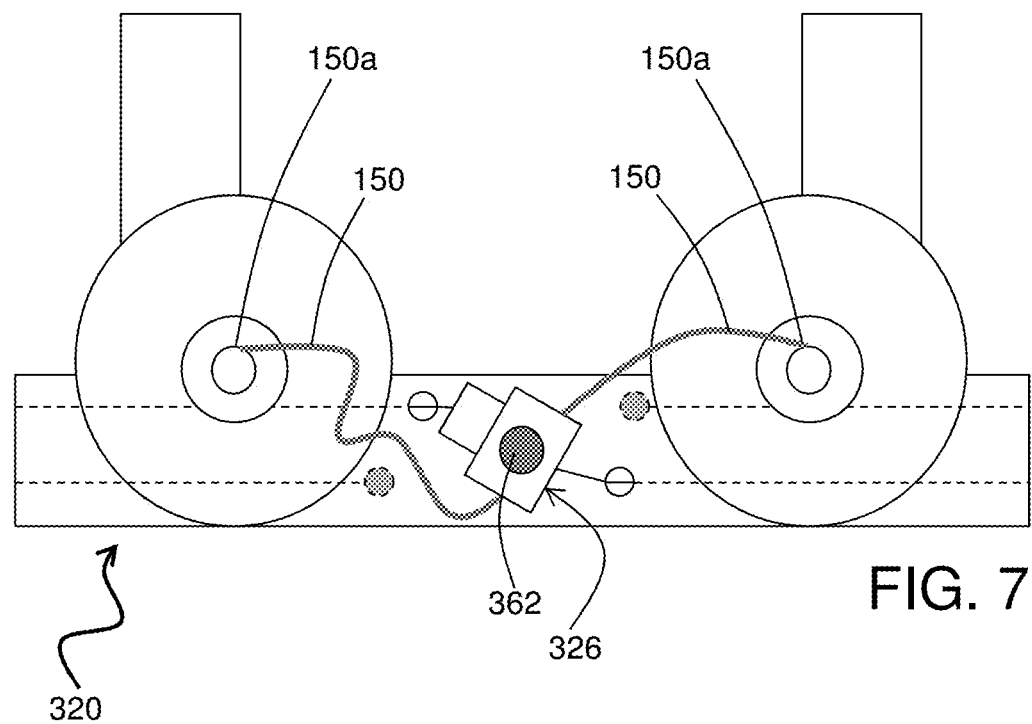
FIG. 7 illustrates another example wearable machine system with a vacuum breaker.

FIG. 7 illustrates another example wearable machine system 320 that is identical to the system 120-1 but additionally includes a vacuum breaker 362. The vacuum breaker 362 is operable to vent the pump and thus release the vacuum in the pump, suction lines 150, and suction cups 150*a*. For example, the vacuum breaker 362 may be used to release the suction cups 150*a* from the user/wearer or disable the pump when the system 320 is being worn but the vacuum is not in use. As can be appreciated, the vacuum breaker 362 may also be used in combination with the manual pump assist 260.

Figure 8:
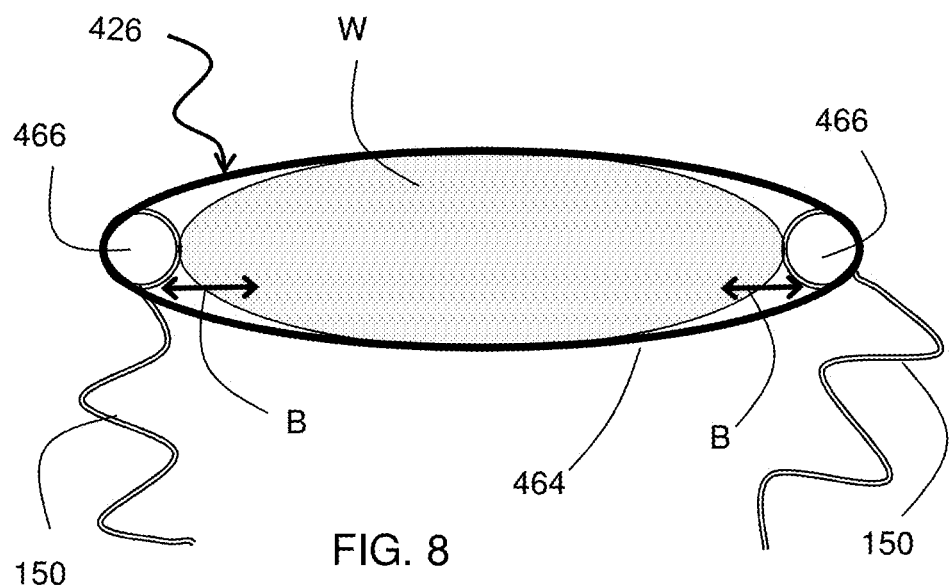
FIG. 8 illustrates an example ball pump machine for a wearable machine system.

FIG. 8 illustrates another example of a machine 426 that can be used in any of the systems described herein. In this example, the machine 426 is a ball pump actuator that includes a semi-rigid shell 464 with one or more ball pumps 466 (two shown). As the wearer W breathes, the expansion of the wearer W collapses the ball pumps 466 against the shell 464 and forces air from the interior of the ball pumps through suction lines 150. The air may be vented from the suction lines 150 to the surroundings through one-way valves or the like. Upon contraction of the wearer W, the ball pumps resiliently expand, thus drawing a vacuum through suction lines 150.

Figure 9:
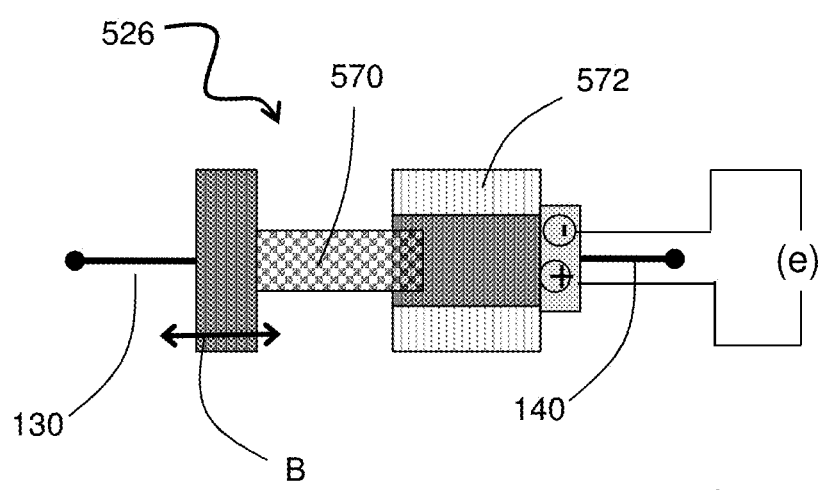
FIG. 9 illustrates an example electrical generator machine for a wearable machine system.

FIG. 9 illustrates another example of a machine 526 that can be used in any of the systems described herein. In this example, the machine 526 is an electrical generator. As can be appreciated, the electrical generator may be of a suitable size for mounting on the garment 22, for example, but may alternatively be mounted elsewhere on the user. The generator includes a magnetic core 570 and a coil 572. In this example, the first cord 130 is connected to the core 570 and the second cord 140 is connected to the coil 572 such that the cords 130/140 repeatedly move the core 570 into and out of the coil 572 with the involuntary movement of the wearer W. Optionally, the bias member 156 can be used to return the core 570 to a home position. Of course, the cords 130/140 could alternatively be reversed with regard to connection to the core 570 and coil 572. The movement generates a current in the coil 572, which may be used to power a load, such as a light or other electronic device on the wearer W.

In a further example, the systems herein may be adapted with the generator to be used as a wearable electrical system that thus includes a flexible actuator that is adapted to wrap at least partially around, and conform with, the shape of a wearer W, and resiliently stretch with involuntary movements of the wearer. The generator is coupled to be mechanically driven by the flexible actuator such that the involuntary movements of the wearer generate electric current through the flexible actuator.

Figure 10:
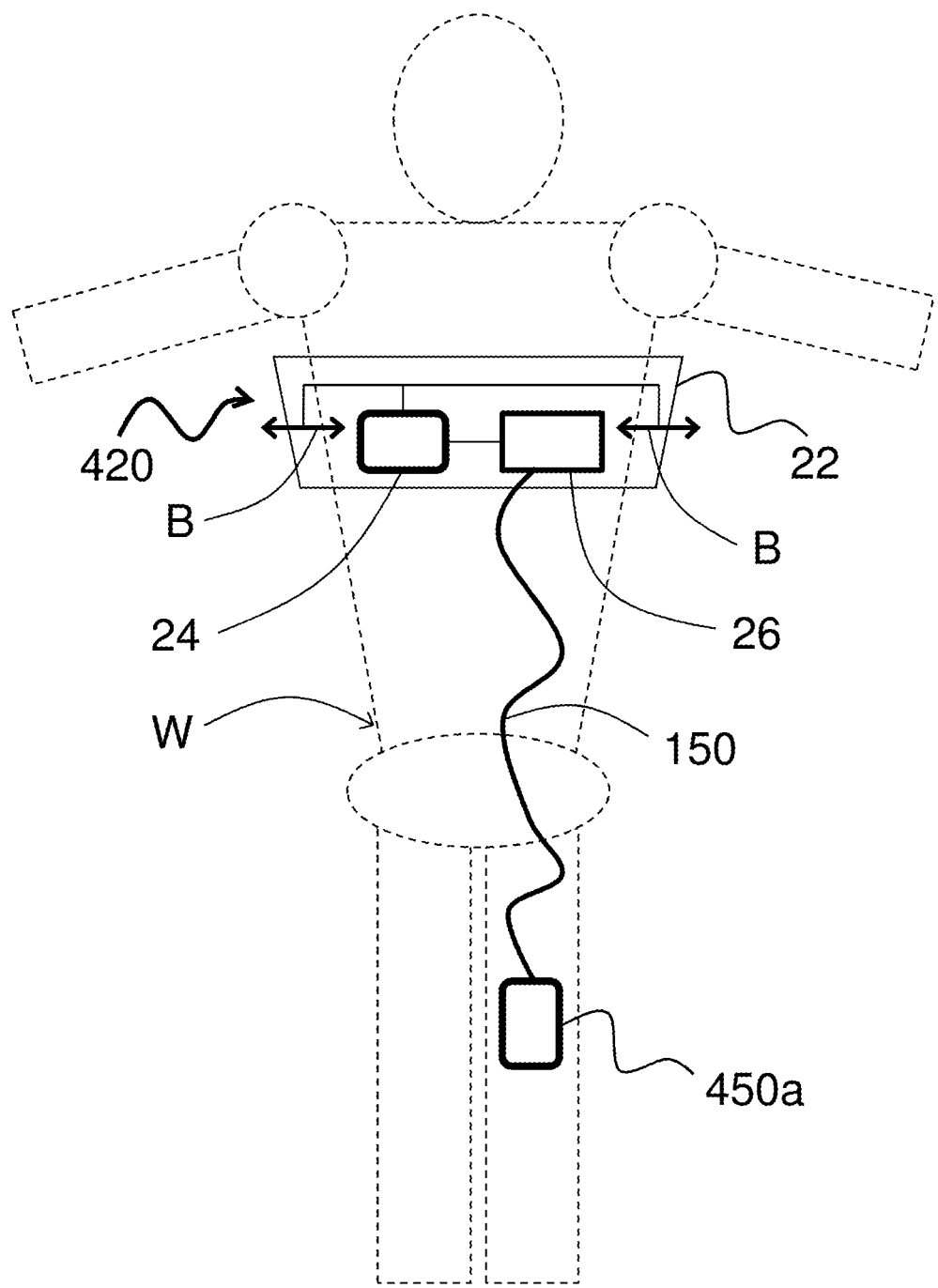
FIG. 10 illustrates another example wearable machine system based on a pump for negative-pressure wound therapy.

FIG. 10 illustrates another example wearable machine system 420 that is configured for negative-pressure wound therapy. In this example, a single suction line 150 extends from the machine 26 (vacuum pump) to a suction cup 450*a*. The suction cup 450*a* can be adapted in shape for the particular type of wound being treated. The involuntary breathing movement of the wearer W powers the pump and generates a negative pressure in the suction cup 450*a*, to facilitate healing at the wound site.

Also disclosed is a method of powering a machine. For example, the method may include wrapping a flexible actuator at least partially around a wearer W such that the flexible actuator is in conformance with the shape of the wearer, and powering a machine that is coupled to the flexible actuator by resiliently stretching the flexible actuator with involuntary movements of the wearer. For instance, the flexible actuator may be or may include the garment 22 disclosed herein above, the passive actuator 24, or a combination thereof.

Although a combination of features is shown in the illustrated examples, not all of them need to be combined to realize the benefits of various embodiments of this disclosure. In other words, a system designed according to an embodiment of this disclosure will not necessarily include all of the features shown in any one of the figures or all of the portions schematically shown in the figures. Moreover, selected features of one example embodiment may be combined with selected features of other example embodiments.

The preceding description is exemplary rather than limiting in nature. Variations and modifications to the disclosed examples may become apparent to those skilled in the art that do not necessarily depart from this disclosure. The scope of legal protection given to this disclosure can only be determined by studying the following claims.

What is claimed is:

1. A wearable machine system comprising:
   a garment;
   a passive actuator mounted to the garment, the passive actuator being actuatable responsive to involuntary expansion and contraction breathing movements of a wearer of the garment;
   a machine coupled with the passive actuator such that actuation of the passive actuator, responsive to the involuntary expansion and contraction breathing movements, mechanically drives the machine, wherein the machine includes a vacuum pump, and a suction line and a suction cup attached with the vacuum pump, and actuation of the vacuum pump upon expansion breathing movement causing a negative pressure in the suction line and suction cup; and
   a ball pump actuator also connected with the suction cup, the ball pump actuator including a semi-rigid shell and a ball pump, the ball pump collapsing against the semi-rigid shell with expansion breathing movement to force air from an interior of the ball pump through a vent valve, and the ball pump expanding with contraction breathing movement and causing a negative pressure in the suction line and suction cup.

2. The wearable machine system as recited in claim 1, wherein the passive actuator includes a cord mounted on the garment, the cord having first and second ends spanned by a cord length, the first end being fixed to the garment at a fixed anchor point on a front of the garment, the cord extending around the garment to a pivot on a back of the garment, looping around the pivot, and then extending back around to the front of the garment, and the second end being coupled to the machine such that the involuntary movement causes the cord to actuate the machine.

3. The wearable machine system as recited in claim 2, wherein the garment includes an elongated strap having opposed, connectable ends, and the cord runs in the elongated direction of the elongated strap.

4. The wearable machine system as recited in claim 3, wherein the anchor point is in a middle one-third of the strap.

5. The wearable machine system as recited in claim 2, wherein the cord includes a wire and a sheathing, the wire being translatable inside the sheathing.

6. The wearable machine system as recited in claim 1, wherein the passive actuator includes a cord mounted on the garment, the cord having first and second ends spanned by a cord length, the first end being coupled to a first portion of the machine and the second end being coupled to a second portion of the machine such that the involuntary movement causes the cord to actuate the machine.

7. The wearable machine system as recited in claim 1, wherein the passive actuator includes first and second cords mounted on the garment, the first and second cords each including first and second ends spanned by a cord length, the first end being fixed to the garment at an anchor point, the cord length wrapping at least partially around the wearer, and the second end being connected to the machine, the respective cord lengths wrapping in opposite directions around the wearer such that the involuntary movements cause the first and second cords to cooperatively actuate the machine.

8. The wearable machine system as recited in claim 7, wherein the respective first ends of the first and second cords are fixed at a common anchor point.

9. The wearable machine system as recited in claim 1, further comprising a drain line and a reservoir, the drain line opening at one end to the suction cup and opening at an opposed end to the reservoir.

10. The wearable machine system as recited in claim 1, wherein the involuntary movements are breathing expansion/contraction.

11. The wearable machine system as recited in claim 1, wherein the garment is resilient and adapted to conform to the shape of the wearer.

12. The wearable machine system as recited in claim 1, wherein the machine includes a bias member biasing the machine to a home position such that upon actuation of the machine by the passive actuator away from the home position, the biasing member moves the machine back toward the home position.

13. A wearable machine system comprising:
    a flexible actuator adapted to:
       wrap at least partially around, and conform with, the shape of a wearer and resiliently stretch with involuntary breathing movements of the wearer;
    a machine coupled to be driven by the flexible actuator such that the involuntary movements of the wearer power the machine through the flexible actuator, wherein the machine includes a vacuum pump, and a suction line and a suction cup attached with the vacuum pump, and actuation of the vacuum pump upon expansion breathing movement causing a negative pressure in the suction line and suction cup; and
    a ball pump actuator also connected with the suction cup, the ball pump actuator including a semi-rigid shell and a ball pump, the ball pump collapsing against the semi-rigid shell with expansion breathing movement to force air from an interior of the ball pump through a vent valve, and the ball pump expanding with contraction breathing movement and causing a negative pressure in the suction line and suction cup.

14. The wearable machine system as recited in claim 13, wherein the involuntary movements of the wearer exclusively power the machine.

15. The wearable machine system as recited in claim 13, wherein the flexible actuator includes a flexible garment with at least one translatable cord that is connected to the machine.

16. The wearable machine system as recited in claim 1, wherein the machine includes a plunger coupled with the passive actuator and a bias member biasing the plunger toward a home position, wherein actuation of the passive actuator extends the plunger and the bias member retracts the plunger to the home position.

17. The wearable machine system as recited in claim 16, further comprising an additional suction line and an additional suction cup attached with the vacuum pump, and the machine is located on the garment and is between the suction cup and the additional suction cup.

18. The wearable machine system as recited in claim 17, wherein the passive actuator includes a cord mounted on the garment, the cord having first and second ends spanned by a cord length, the first end being fixed to the garment at a fixed anchor point on a front of the garment, the cord extending around the garment to a pivot on a back of the garment, looping around the pivot, and then extending back around to the front of the garment, and the second end being coupled to the machine such that the involuntary movement causes the cord to actuate the machine.

19. The wearable machine system as recited in claim 17, wherein the machine includes a vacuum breaker.

\* \* \* \* \*